(12) United States Patent
Schaffer

(10) Patent No.: US 7,989,703 B2
(45) Date of Patent: Aug. 2, 2011

(54) ALTERNATING CORE COMPOSITE WIRE

(75) Inventor: Jeremy E. Schaffer, Leo, IN (US)

(73) Assignee: Fort Wayne Metals Research Products Corporation, Fort Wayne, IN (US)

( * ) Notice: Subject to any disclaimer, the term of this patent is extended or adjusted under 35 U.S.C. 154(b) by 1 day.

(21) Appl. No.: 12/395,090

(22) Filed: Feb. 27, 2009

(65) Prior Publication Data

US 2009/0260852 A1    Oct. 22, 2009

Related U.S. Application Data

(60) Provisional application No. 61/032,508, filed on Feb. 29, 2008.

(51) Int. Cl.
*H01B 5/00* (2006.01)
(52) U.S. Cl. .................................................. 174/126.2
(58) Field of Classification Search ............... 174/117 F, 174/117 FF, 126.2, 129 S
See application file for complete search history.

(56) References Cited

U.S. PATENT DOCUMENTS

| | | | |
|---|---|---|---|
| 3,045,199 A | 7/1962 | Shobert, II | |
| 3,646,322 A | 2/1972 | Speekman | |
| 3,662,222 A | 5/1972 | Ray | |
| 3,666,879 A | 5/1972 | Hirsch et al. | |
| 3,698,394 A | 10/1972 | Piper et al. | |
| 4,103,276 A | 7/1978 | Kennon et al. | |
| 4,240,026 A | 12/1980 | Murphy et al. | |
| 4,709,699 A | 12/1987 | Michael et al. | |
| 4,826,091 A | 5/1989 | Legatos et al. | |
| 5,201,740 A | 4/1993 | Nakao et al. | |
| 5,520,194 A | 5/1996 | Miyata et al. | |
| 5,596,996 A | 1/1997 | Johanson et al. | |

(Continued)

FOREIGN PATENT DOCUMENTS

JP    74015350 B    4/1974

OTHER PUBLICATIONS

Written Opinion and International Search Report mailed May 11, 2009 in related International Application No. PCT/US2009/035514.

(Continued)

*Primary Examiner* — Chau N Nguyen
(74) *Attorney, Agent, or Firm* — Baker & Daniels LLP

(57) ABSTRACT

A wire having an outer shell and a core, the core including at least a first plurality of core segments that may be made of a first core material and a second plurality of core segments that may be made of a second core material different from the first core material. The first and second core segments are arranged in a periodic alternating arrangement along the length of the wire. The outer shell may be made of a metal, such as a biocompatible metal, and the core segments may be made of different materials to provide periodic material properties along the length of the wire. The wire is manufactured by inserting the core segments into the outer shell to form a wire construct, followed by subjecting the wire construct to one or more initial draws while applying a compressive force to the core segments on an upstream side of the die to maintain the core segments in contact with one another upon dense contact between the outer shell and core segments, following by closing of the outer shell onto the core segments, as the wire is pulled through a drawing die. The resulting wire may then be subjected to a plurality of finishing draws. Exemplary applications of the wire include medical devices, such as in vivo heating devices, thermally-actuated snares, in vivo positioning devices, stents, and tissue scaffolds.

22 Claims, 11 Drawing Sheets

U.S. PATENT DOCUMENTS

| | | | |
|---|---|---|---|
| 5,931,819 | A | 8/1999 | Fariabi |
| 6,019,736 | A | 2/2000 | Avellanet et al. |
| 6,287,306 | B1 | 9/2001 | Kroll et al. |
| 6,388,194 | B1 | 5/2002 | Ryeczek |
| 6,488,637 | B1 | 12/2002 | Eder et al. |
| 6,524,301 | B1 | 2/2003 | Wilson et al. |
| 6,638,266 | B2 | 10/2003 | Wilson et al. |
| 7,020,947 | B2 | 4/2006 | Bradley |
| 7,097,624 | B2 | 8/2006 | Campion et al. |
| 7,115,125 | B2 | 10/2006 | Nakao et al. |
| 7,147,660 | B2 | 12/2006 | Chobotov et al. |
| 7,163,533 | B2 | 1/2007 | Hobbs et al. |
| 7,179,257 | B2 | 2/2007 | West et al. |
| 7,179,291 | B2 | 2/2007 | Rourke et al. |
| 7,182,756 | B2 | 2/2007 | Saeed et al. |
| 7,186,223 | B2 | 3/2007 | Hiejima et al. |
| 7,188,473 | B1 | 3/2007 | Asada et al. |
| 7,189,254 | B2 | 3/2007 | Magers |
| 7,420,124 | B2 | 9/2008 | Michael et al. |
| 7,490,396 | B2 | 2/2009 | Bradley |
| 2004/0260206 | A1 | 12/2004 | Murayama et al. |
| 2006/0047223 | A1 | 3/2006 | Grandfield et al. |
| 2006/0106443 | A1 | 5/2006 | Michael et al. |
| 2006/0106444 | A1 | 5/2006 | Michael et al. |
| 2007/0060846 | A1 | 3/2007 | Hardin |
| 2008/0091169 | A1 | 4/2008 | Heideman et al. |
| 2009/0024110 | A1 | 1/2009 | Heideman et al. |

OTHER PUBLICATIONS

International Preliminary Report on Patentability mailed Sep. 10, 2010 in related International application No. PCT/US2009/035514.
Written Opinion and International Search Report mailed May 11, 2009 in related International application No. PCT/US2009/035514.

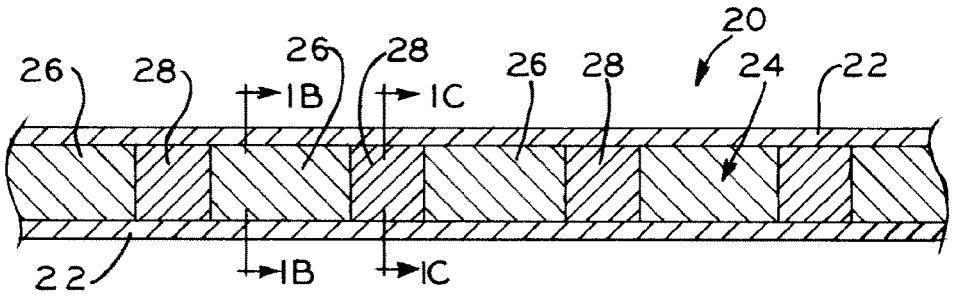
FIG_1A
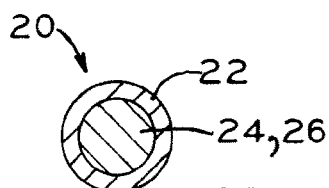
FIG_1B
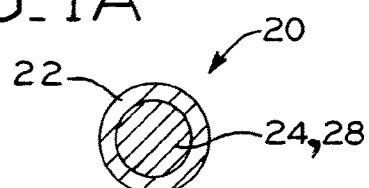
FIG_1C
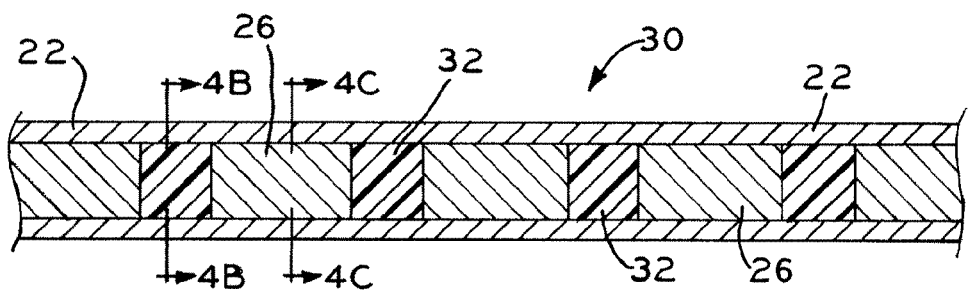
FIG_4A
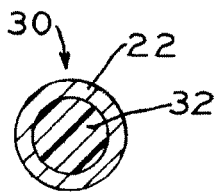
FIG_4B
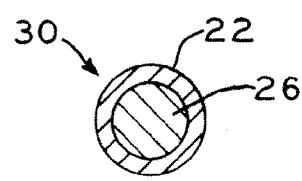
FIG_4C

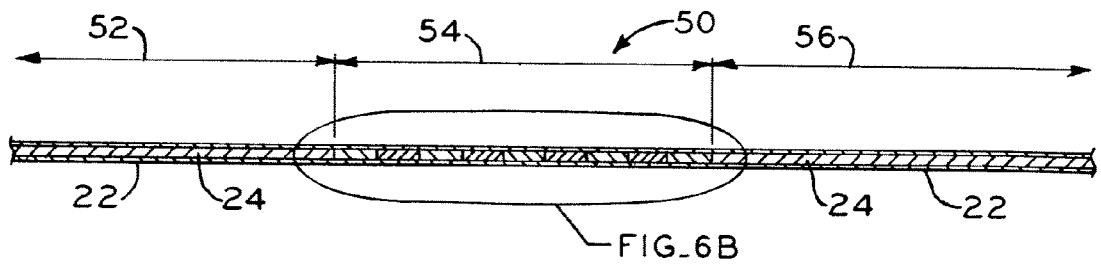
FIG_6A
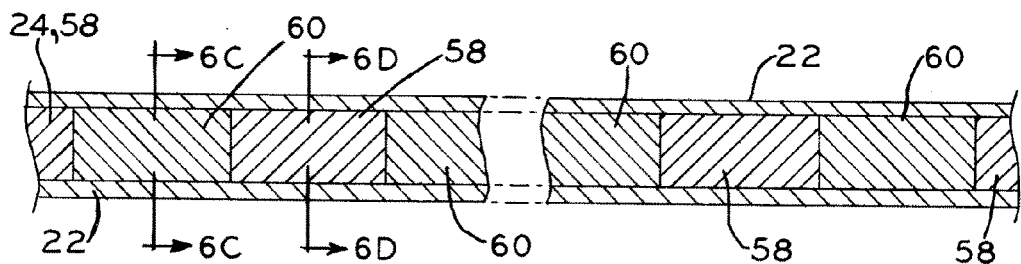
FIG_6B
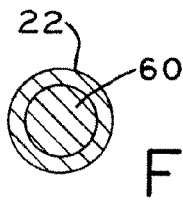
FIG_6C
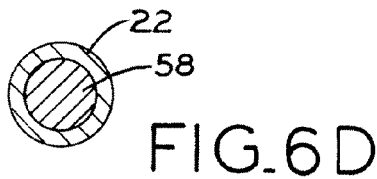
FIG_6D
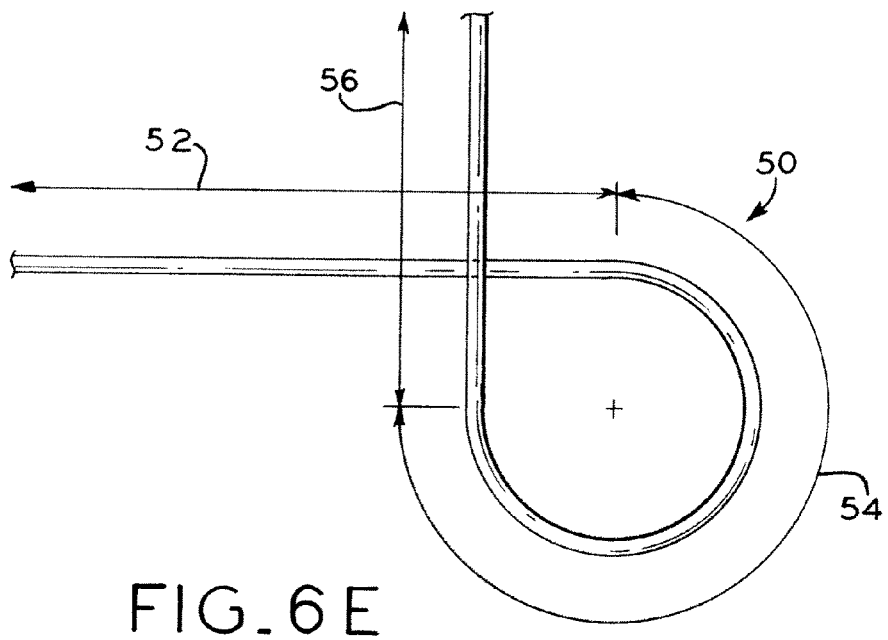
FIG_6E

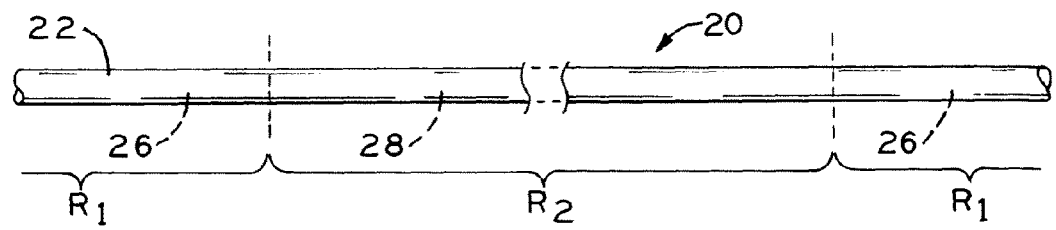
FIG_7
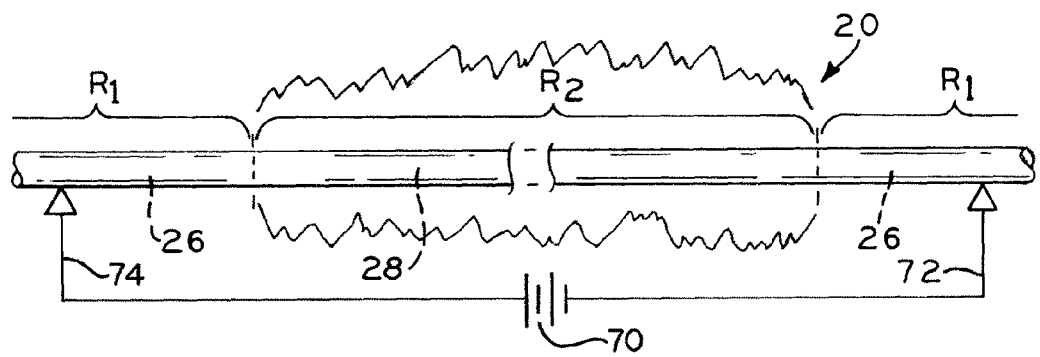
FIG_8
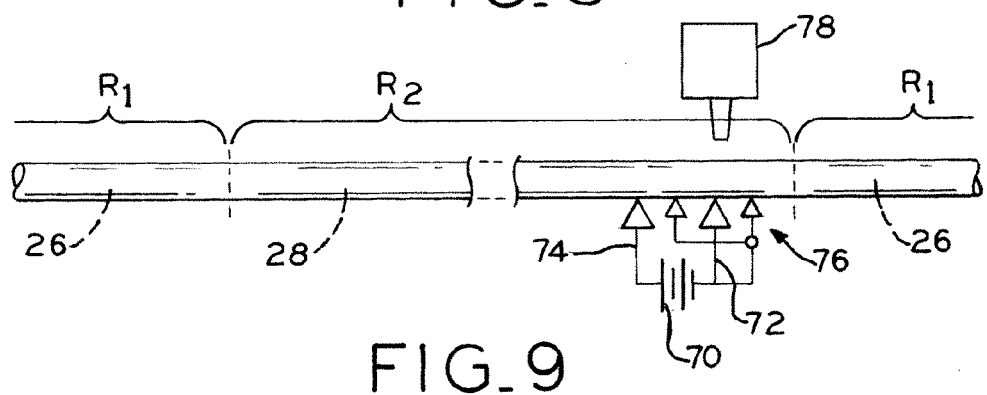
FIG_9

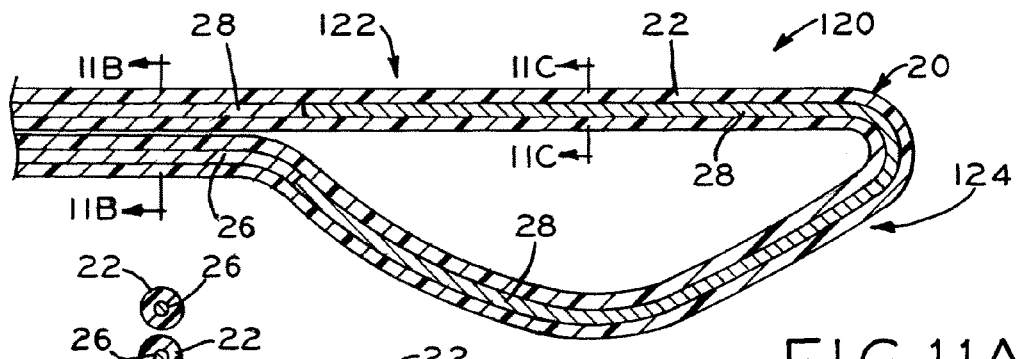
FIG.11A
FIG.11B
FIG.11C
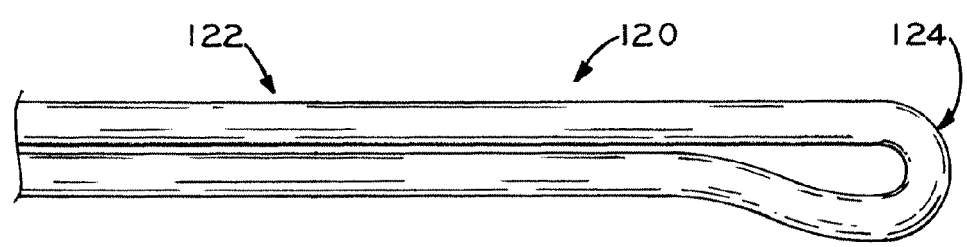
FIG.11D
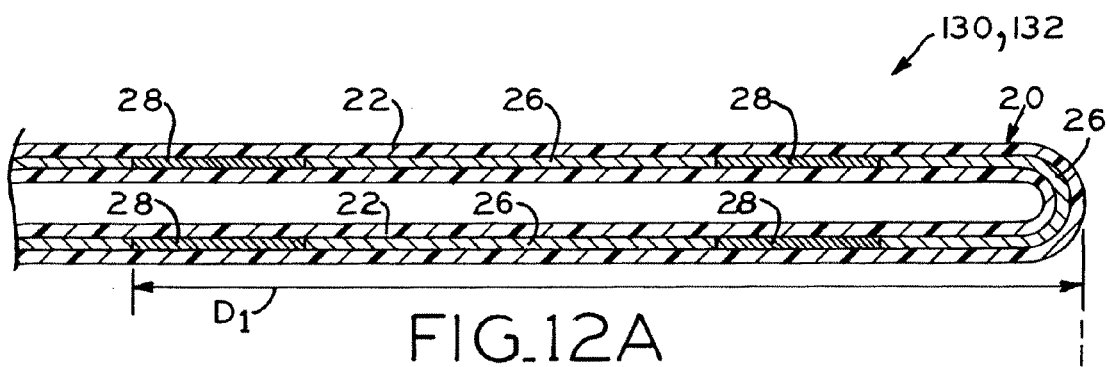
FIG.12A
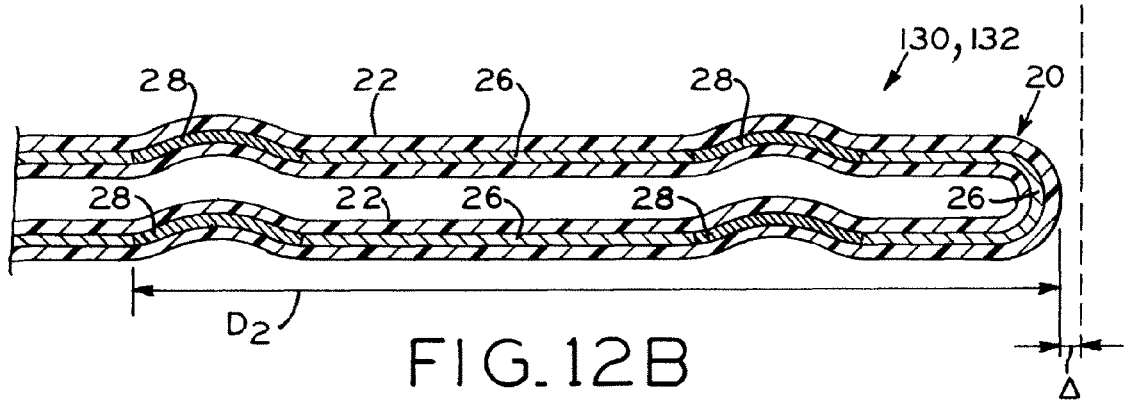
FIG.12B

ALTERNATING CORE COMPOSITE WIRE

CROSS REFERENCE TO RELATED APPLICATIONS

This application claims the benefit under Title 35, U.S.C. §119(e) of U.S. Provisional Patent Application Ser. No. 61/032,508, entitled ALTERNATING CORE COMPOSITE WIRE, filed on Feb. 29, 2008, the disclosure of which is expressly incorporated by reference herein.

BACKGROUND OF THE INVENTION

1. Field of the Invention

The present invention relates to a wire having an outer shell and a core disposed within the outer shell, the wire being manufactured via a drawing process and useful in medical applications, for example.

2. Description of the Related Art

Medical grade wires, and medical leads and/or devices that include medical grade wires, are disclosed in U.S. patent application Ser. Nos. 10/524,387 and 11/203,986, published as U.S. Patent Application Publication Nos. 2006/0106443 and 2006/0106444, respectively, each assigned to the assignee of the present application, the disclosures of which are expressly incorporated herein by reference.

These wires generally include a metal outer shell and a core disposed within the outer shell. The outer shell and the core are each made of biocompatible metals and, in some embodiments, the core may include a plurality of twisted wire strand elements each including a metallic tube filled with a metal. To manufacture the wire, the wire strand elements are inserted within the outer shell to form a wire construct, followed by drawing the wire construct down to reduce the diameter of the wire construct, wherein the wire strand elements are compacted together within the outer shell such that substantially no voids exist within the outer shell. Optionally, the drawn wire may be coated with an insulation layer and incorporated into a medical device, such as a medical lead, for example.

In this manner, the wire includes an outer shell containing a plurality of wire elements that may be differently constructed for providing different properties to the wire. These types of wires will have the same construction, in cross section, along their entire length.

SUMMARY OF THE INVENTION

The present invention provides a wire having an outer shell and a core, the core including at least a first plurality of core segments that may be made of a first core material and a second plurality of core segments that may be made of a second core material different from the first core material. The first and second core segments are arranged in a periodic alternating arrangement along the length of the wire. The outer shell may be made of a metal, such as a biocompatible metal, and the core segments may be made of different materials to provide periodic material properties along the length of the wire. The wire is manufactured by inserting the core segments into the outer shell to form a wire construct, followed by subjecting the wire construct to one or more initial draws while applying a compressive force to the core segments on an upstream side of the die to maintain the core segments in contact with one another upon dense contact between the outer shell and core segments, following by closing of the outer shell onto the core segments, as the wire is pulled through a drawing die. The resulting wire may then be subjected to a plurality of finishing draws.

In one embodiment, the core segments may be formed of first and second metals having different properties such as atomic weight, shape memory, or electrical resistance, for example. In another embodiment, the core segments may be formed of one or more metals together with one or more polymeric materials to provide differing properties such as electrical resistance or radiofrequency-opacity, for example. Also disclosed is a method for selectively marking the outer shell to indicate the presence of certain core sections along the length of the wire.

In one form thereof, the present invention provides a wire, including an outer shell made of a biocompatible metal; and a core disposed within the outer shell, the core including a plurality of first core segments made of a first material and at least one second core segment made of a second material different from the first material, the first and second core segments arranged in a periodic alternating arrangement along a length of the wire.

In another form thereof, the present invention provides a method of manufacturing a wire, including the steps of: providing an outer shell made of a biocompatible metal; inserting a plurality of first core segments and at least one second core segment into the outer shell to form a wire construct, the first and second core segments disposed in a periodic alternating arrangement along a length of the outer shell; and drawing the wire construct from a first outer diameter to a second outer diameter less than the first outer diameter.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1A is longitudinal sectional view of a portion of a wire in accordance with a first embodiment of the present invention;

FIG. 1B is a cross sectional view taken along line 1B-1B of FIG. 1;

FIG. 1C is a cross sectional view taken along line 1C-1C of FIG. 1;

FIG. 4A is longitudinal sectional view of a portion of a wire in accordance with a second embodiment of the present invention;

FIG. 4B is a cross sectional view taken along line 4B-4B of FIG. 4A;

FIG. 4C is a cross sectional view taken along line 4C-4C of FIG. 4A;

FIG. 6A is a view of a portion of a wire in accordance with a fourth embodiment of the present invention, shown in a first orientation;

FIG. 6B is longitudinal sectional view of a portion of the wire of FIG. 6A;

FIG. 6C is a cross sectional view taken along line 6C-6C of FIG. 6B;

FIG. 6D is a cross sectional view taken along line 6D-6D of FIG. 6B;

FIG. 6E is a view of a portion of a wire in accordance with a fourth embodiment of the present invention, shown in a second orientation;

FIG. 7 is a view of a portion of a wire including a core made of different core segments;

FIG. 8 is a view illustrating a first exemplary method of marking the outer shell of the wire of FIG. 7 to indicate the location of one or more of the core segments thereof;

FIG. 9 is a view illustrating a second exemplary method of marking the outer shell of the wire of FIG. 7 to indicate the location of one or more of the core segments thereof;

FIG. 11A is a longitudinal sectional view of a thermally activated snare device including a wire made in accordance with the present invention, shown in a relatively low temperature state;

FIG. 11B is a sectional view taken along line 11B-11B of FIG. 11A;

FIG. 11C is a sectional view taken along line 11C-11C of FIG. 11A;

FIG. 11D is a perspective view of the device of FIG. 11A, shown in a relatively high temperature state;

FIG. 12A is a longitudinal sectional view of a thermally activated linear motion device for in vivo positioning or mechanical actuation, including a wire made in accordance with the present invention, shown in a relatively low temperature state;

FIG. 12B is a longitudinal sectional view of the device of FIG. 12A, shown in a relatively high temperature state;

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION

Figure 2A:
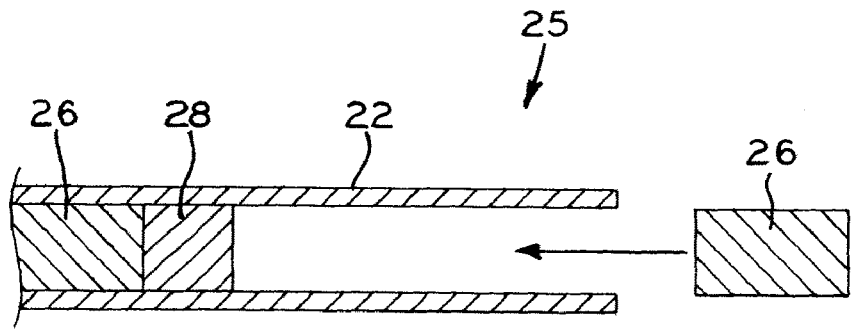
FIG. 2A is a longitudinal sectional view through an outer shell, showing insertion of core segments within the outer shell to form a wire construct.

Referring to FIGS. 1A-C, wire 20 is shown in accordance with a first embodiment of the present invention, referred to herein as an alternating core composite wire, which generally defines a longitudinal axis and a desired length, and includes outer shell 22 and core 24. Outer tube or shell 22 is formed as a tube and may be made of a metal such as stainless steel and, in particular, other biocompatible metals such as titanium, titanium alloys, cobalt-nickel-chromium alloys, nitinol, platinum, platinum alloys, tantalum, and tantalum alloys, for example. Outer shell 22 may be formed as a uniform and continuous surface or jacket, such that wire 20 may be coiled, braided, or stranded as desired.

Specific materials for outer shell 22 include ASTM F562 cobalt-nickel-chromium alloys, such as MP35N® and 35N LT®, available from Fort Wayne Metals Research Products Corp. of Fort Wayne, Ind., including the materials disclosed in U.S. patent application Ser. No. 10/656,918 (published as U.S. Patent Application Publication No. 2005/0051243), entitled "cobalt-chromium-nickel-molybdenum alloys with reduced level of titanium nitride inclusions", assigned to the assignee of the present application, the disclosure of which is expressly incorporated herein by reference. Other suitable materials for outer shell 22 include ASTM F1058 cobalt-chromium-nickel-molybdenum-iron alloys, such as FWM 1058™, nickel-titanium shape memory alloys, such as NiTiNOL, cobalt-nickel-chromium-tungsten-iron-manganese alloy, such as L605 alloy, 300 series stainless steels or other similar metals also available from Fort Wayne Metals Research Products Corp. of Fort Wayne, Ind.

Core 24 includes a first plurality of core segments 26 made of a first material and a second plurality of core segments 28 made of a second material. As may be seen in FIGS. 1A-1C, first and second core segments 26 and 28 are disposed in a periodic alternating arrangement along the length of wire 20. The term "periodic alternating arrangement", as used herein, is meant to refer to any arrangements in which a core segment of a first type is followed by a core segment of a second type, and thence by another core segment of the first type, and so on, to form a pattern of [A-B-A-B- . . . ], as well as any other arrangement which demonstrates periodicity along at least a portion of the length of the wire. For example, one alternative arrangement may include one core segment 26 of a first type followed by two or more core segments of a second type to form a pattern of [A-B-B-A-B-B- . . . ]. Other exemplary patterns include [A-B-C-A-B-C- . . . ], [A-A-B-B- . . . ], [A-B-C-D-A-B-C-D- . . . ], and [A-B-A-B-C-A-B-A-B-C- . . . ], etc.

In this regard, the specific arrangement of the alternating first and second core segments 26 and 28 and/or additional core segments may vary, so long as at least some periodicity, or repeating pattern, is present along at least a portion of the wire. Also, the lengths of first and second core segments 26 and 28 along the longitudinal axis of wire 20 may vary, either with respect to individual core segments 26 or 28 themselves, or between core segments 26 and core segments 28, for example. As described below, this feature allows specific and desirable mechanical, electrical, chemical, and/or other properties to be imparted in a periodic arrangement along the length of wire 20.

In one embodiment, the material of first core segments 26 differs from the material of second core segments 28, and first and second core segments 26 and 28 may be made of the metals set forth above with respect to outer shell 22, and/or may be made of other metals such as iron, silver, copper, gold, etc.

Figure 2B:
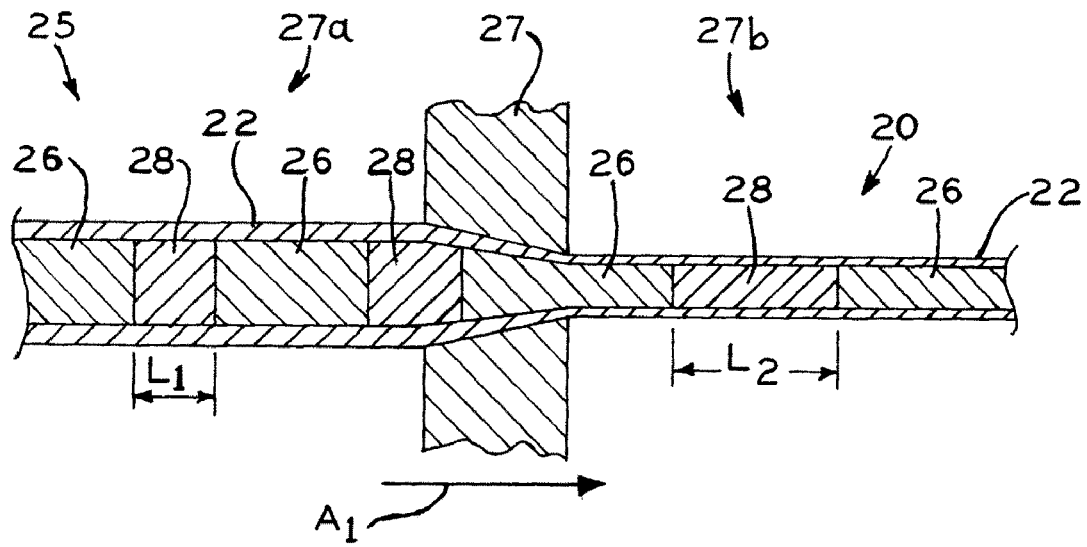
FIG. 2B is a longitudinal sectional view through a die, showing the drawing of the wire construct of FIG. 2A.

Wire 20 may be made in one embodiment via a process generally illustrated in FIGS. 2A and 2B, and which is described in further detail below in connection with FIGS. 3A-3C. In a first step, an outer shell 22 having a first diameter is provided, which is subsequently filled with a desired number and arrangement of core segments, such as first and second core segments 26 and 28 in an alternating pattern as shown, to form a wire construct 25, as shown in FIG. 2A. Thereafter, as shown in FIG. 2B, the wire construct 25 is drawn through a lubricated die 27 from an upstream side 27a of the die to a downstream side 27b of the die along a draw direction indicated by arrow $A_1$ to reduce the diameter of wire construct 25 from the first diameter to a second, lesser diameter while compacting core segments 26 and 28 such that the outer diameters of core segments 26 and 28 is equal to the inner diameter of outer shell 22. In this manner, when viewed in section as in FIGS. 1B and 1C, for example, each of the core segments 26 and 28 completely fills the outer shell 22 with no voids present therebetween. As also shown in FIG. 2B, the drawing of wire construct 25 results in a length increase of outer shell 22, and a corresponding length increase in core segments 26 and 28 along the direction of outer shell 22 from an initial length $L_1$ to a final length $L_2$, which is proportionate to the diameter reduction, as discussed in detail below. Optionally, either before or after drawing, or in place thereof, wire 20 may be processed by hot working, annealing, cleaning, coiling, braiding, and/or cabling, for example.

Figure 3A:
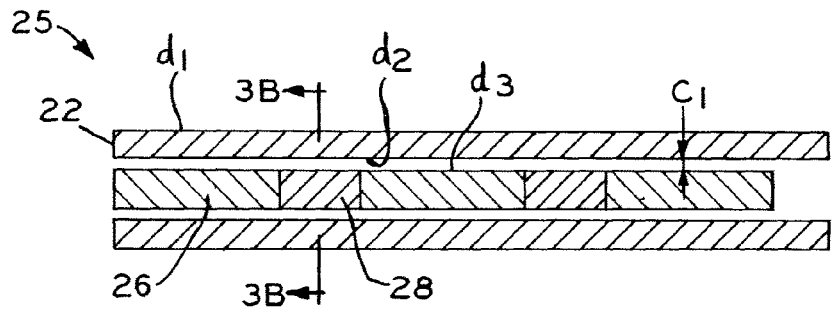
FIG. 3A is a longitudinal sectional view through a wire construct showing the initial clearance between the outer shell and the core segments.
Figure 3B:
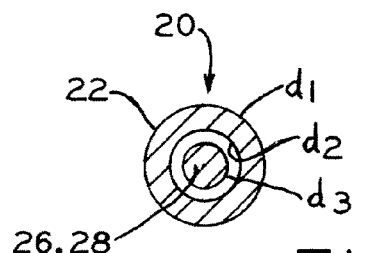
FIG. 3B is a sectional view taken along line 3B-3B of FIG. 3A.
Figure 3C:
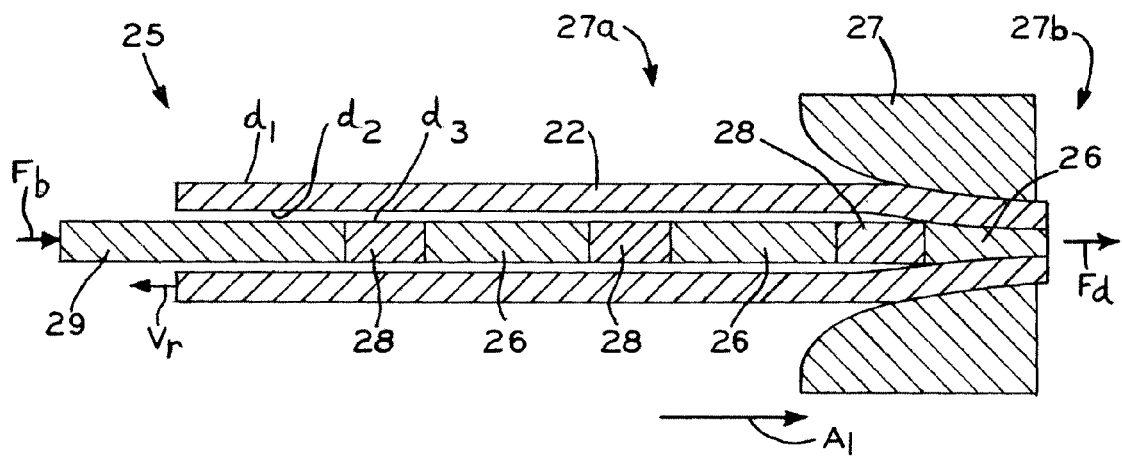
FIG. 3C is a longitudinal sectional view through a die, showing the drawing of the wire construct of FIG. 3A using a back support rod.
Figure 5A:
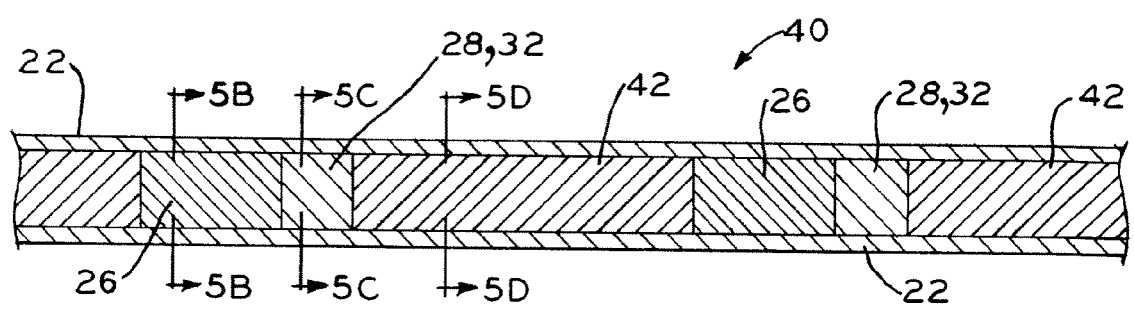
FIG. 5A is a longitudinal sectional view of a portion of a wire in accordance with a third embodiment of the present invention.
Figure 5B:
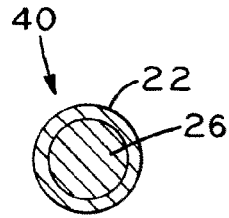
FIG. 5B is a cross sectional view taken along line 5B-5B of FIG. 5A.
Figure 5C:
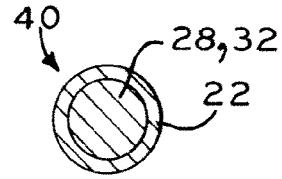
FIG. 5C is a cross sectional view taken along line 5C-5C of FIG. 5A.
Figure 5D:
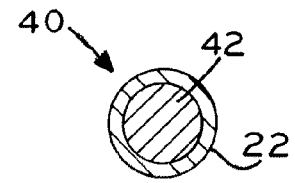
FIG. 5D is a cross sectional view taken along line 5D-5D of FIG. 5A.
Figure 10A:
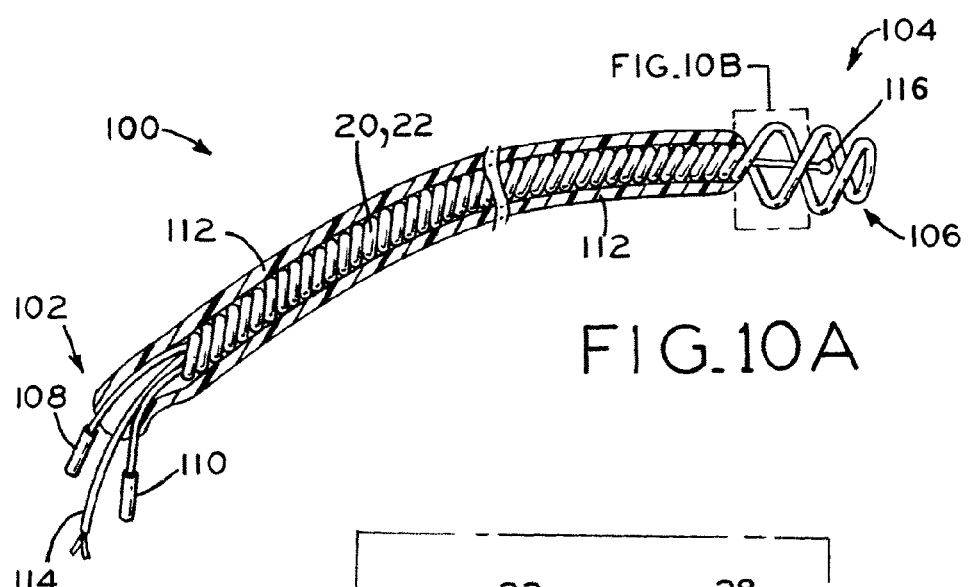
FIG. 10A is a longitudinal sectional view of an in vivo heating apparatus including a wire made in accordance with the present invention.
Figure 10B:
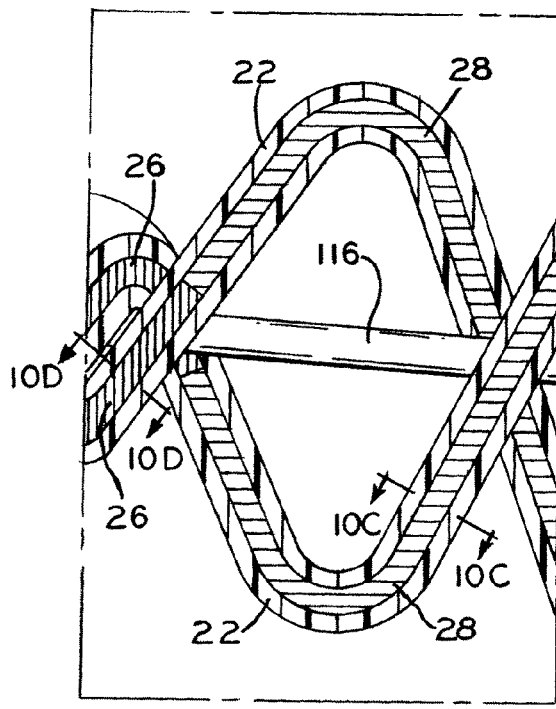
FIG. 10B is a fragmentary sectional view of a portion of the distal end of the apparatus of FIG. 10A.
Figure 10C:
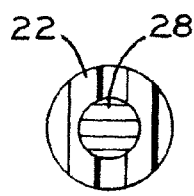
FIG. 10C is a sectional view taken along line 10C-10C of FIG. 10B.
Figure 10D:
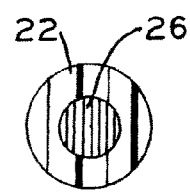
FIG. 10D is a sectional view taken along line 10D-10D of FIG. 10B.

With reference to FIGS. 3A-3C, the drawing of a wire construct 25 to form wire 20 is described in further detail. In particular, as described below, wire construct 25 may be drawn in a manner which ensures that each of the core segments, such as core segments 26 and 28, are maintained in abutting contact with one another to provide a uniform periodicity of the core segments within the drawn wire.

Referring to FIGS. 3A and 3B, outer shell 22 of wire construct 25 includes outer diameter $d_1$ and inner diameter $d_2$, and core segments 26 and 28 include outer diameter $d_3$. Once core segments 26 and 28 are loaded into outer shell 22 as shown in FIG. 2A and described above to form wire construct 25, there will be a small clearance between inner diameter $d_2$ of outer shell 22 and outer diameter $d_3$ of core segments 26 and 28, designated $c_1$ in FIG. 3A. This clearance $c_1$ may vary between the core segments, for example, if core segments 26 and 28 have different outer diameters $d_3$.

As described below, when wire 20 is subjected to one or more initial draws, due to the presence of the clearance $c_1$ there will be an initial reduction in the outer diameter $d_1$, and a corresponding length increase, of outer shell 22 prior to contact of the inner diameter $d_2$ of outer shell 22 with core segments 26 and 28. Thereafter, upon subsequent initial draws, when outer shell 22 is drawn to a sufficient extent, the inner diameter $d_2$ of outer shell 22 will contact core segments 26 and/or 28, which contact will be referred to hereinafter as dense contact, or the dense contact point. More than one dense contact point may exist, for example, when the outer diameter of core segments 26 and 28 is different, with a first dense contact point occurring when outer shell 22 closes on the core segment having the greater outer diameter $d_3$, and a second dense contact point occurring when outer shell 22 closes on the core segment having the lesser outer diameter $d_3$. Just after dense contact, further reduction of the inner diameter $d_2$ of outer shell 22 will physically secure the outer shell 22 to the core segment 26 or 28, or stated differently, will fix the position of, or capture, the core segment 26 or 28 within the outer shell, and will also begin to reduce the outer diameter $d_3$ of the core segments 26 or 28. This will be referred to hereinafter as closing, or the closing point. The closing point is chosen such that slight reduction of core segments 26 and/or 28 occurs after dense contact.

The length increase of outer shell 22 prior to the dense contact point, the length increase in wire 20 just after the dense contact point and through the closing point, and the length increase in wire 20 following the closing point are each described in detail below.

During round die reduction of the wire, the cross-sectional area of outer shell 22 is reduced, and the length of outer shell 22 increases, at a constant material density. In the initial draws prior to the dense contact point, the length increase ($\Delta$) of the wire is given by formula (I) below:

$$\frac{\text{Start area}}{\text{Final area}} = \Delta = \frac{(d_1^2 - d_2^2)}{(d_{11}^2 - d_{21}^2)} \tag{I}$$

where $d_{11}$ is outer diameter corresponding to $d_1$ of outer shell 22 after drawing, and $d_{21}$ is inner diameter corresponding to $d_2$ of outer shell 22 after drawing.

For a small amount of reduction (<40% by area), and for an outer shell 22 having a relatively thin wall (wall thickness <0.35×$d_1$), die reduction of outer shell 22 in the absence of support from core segments 26 and/or 28 prior to the dense contact point and closing point (known in the art as "sync drawing") results in a final wall thickness that is similar to the initial value, i.e., ($d_1$–$d_2$) is approximately equal to ($d_{11}$–$d_{21}$). Thus, formula (I) may be modified per formula (II) below to give the length increase ($\Delta$) in the initial draws at the point of dense contact:

$$\Delta = \frac{(d_1^2 - d_2^2)}{(d_{11}^2 - d_3^2)} \tag{II}$$

where the extent of drawing is selected such that $d_{21} \leq d_3$.

After the closing point, subsequent finishing draws of the resulting wire 20 will result in a reduction in cross-sectional area, and corresponding increase in length, for both outer shell 22 and core segments 26 and 28 in the same manner as if wire 20 were formed of a continuous, single material of uniform cross-section according to the following formula (III):

$$\Delta = (D/d)^2 \tag{III}$$

where D is the outside diameter after the closing point and d is the outside diameter to which the overall section is drawn.

At the dense contact point and through the closing point, due to the discrete core segments 26 and 28 not being physically joined to one another when initially inserted into outer shell 22, the continuous elongation of outer shell 22 will tend to inconsistently separate core segments 26 and 28, creating gaps between core segments 26 and 28 which could compromise the periodic consistency of the final composite wire. Stated another way, core segments 26 and 28 tend to separate from one another upon entry of each respective core segment into die 27, which separation will be repeated as outer shell 22 makes dense contact with, and then closes, on each core segment upon entering die 27, resulting in gaps between each of the individual core segments. Thus, there is a need to adequately constrain core segments 26 and 28 to overcome wall interface friction between the inner diameter $d_2$ of outer shell 22 and core segments 26 and 28 at the dense contact and through closing.

Referring to FIG. 3C, a solution to this concern is provided by applying continuous compressive force, or back force $F_b$, to the core segments 26 and 28 using a back support rod 29, which ensures that core segments 26 and 28 are maintained in contact with one another throughout the drawing process, both prior to dense contact and through closing. Back support rod 29 applies a back force $F_b$ to core segments 26 and 28 that is sufficient to overcome wall friction between inner shell 22 and core segments 26 and 28, and maintain contact therebetween, until outer shell 22 is deformed by drawing die 27 into contact with core segments 26 and 28 and closes on core segments 26 and 28. A lack of a back force would result in the relative motion between core segments 26 and 28 and outer shell 22, designated $V_r$ in FIG. 3C, to create inconsistent and unpredictable gaps between segments thereby disrupting the designed periodicity. The draw force, $F_d$, is applied to the end of the wire protruding from drawing die 27, which is sized to deform core segments 26 and 28 slightly after dense contact is made, and the reduction in cross sectional area of outer shell 22 and core segments 26 and 28 may range from 0 to 20% after dense contact through closing.

Processing of the wire beyond the closing point then may proceed without the use of back support rod 29 according to standard wire processing techniques, including further draws and anneals, as if wire 20 were formed of a continuous, single material of uniform cross-section.

The above construction, wherein core segments 26 and 28 are disposed in a periodic alternating arrangement, allows wire 20 to exhibit varying property periodicity along its length. In one embodiment, first core segments 26 may be formed of a relatively higher electrical resistance material such as stainless steel, pure iron, tantalum, platinum, etc., and second core segments 28 may be formed of a relatively lower electrical resistance material such as silver, copper, gold, platinum, etc., to provide localized and/or periodic heating along wire 20, which may be useful in medical devices such as cauterization snares for the removal of body tissue, a blood heating device, a heat ablation device, or a device including a heated cutting section.

In another embodiment, core segments 26 may be formed of a relatively higher atomic weight material, such as platinum, other platinum group elements, platinum-iridium, tantalum, gold, tungsten, etc., and second core segments 28 may be formed of a relatively lower atomic weight material, such as stainless steel, silver, or nitinol, etc., to facilitate the location of a medical device via x-ray fluoroscopy, for example.

Referring to FIGS. 4A-C, a wire in accordance with a second embodiment of the present invention is shown. Except as described below, wire 30 is identical or substantially identical to wire 20, and the same reference numerals will be used to indicate identical or substantially identical features therebetween.

In wire 30, core segments 26 are made of a metallic material as described above while core segments 32 are formed of a polymeric material. Suitable polymeric materials include polyethylene, polypropylene, polyether ether ketone (PEEK), aramids including Nylon materials, and polyethylene tetrafluoroethylene (PTFE), for example. Other materials useful for core segments 30 include composite materials, such as fiber-reinforced composite materials including carbon fiber reinforced PTFE, Kevlar fiber reinforced polymers, and metallic fiber reinforced polymers, for example. Otherwise, wire 30 may be manufactured in the same manner as wire 20 described above.

In one embodiment, core segments 32 of polymeric material may be used to provide periodic differences in electrical conductivity or radio-opacity with respect to the metal material of core segments 26 along the length of wire 30.

Referring to FIGS. 5A-D, a wire in accordance with a third embodiment of the present invention is shown. Except as described below, wire 40 is identical or substantially identical to wires 20 and 30, and the same reference numerals will be used to indicate identical or substantially identical features therebetween.

Wire 40 includes core segments 26, 28, and/or 32, as well as core segments 42 made of a third material, such as a suitable metal or polymeric material of the type described above. Three possible configurations for the core segments of wire 40, and their resulting periodic property variations imparted to wire 40, are set forth in Table 1 below:

TABLE 1

| Wire | Material of first core segments 26 | Material of second core segments 28/32 | Material of third core segments 42 |
|---|---|---|---|
| 1 | High atomic weight | Low electrical resistance | High electrical resistance |
| 2 | High mechanical strength | High atomic weight | Low electrical resistance |
| 3 | High electrical resistance | Low electrical resistance | Superelastic or shape memory property |

Referring to FIGS. 6A-E, a wire in accordance with a fourth embodiment of the present invention is shown. Except as described below, wire 50 is identical or substantially identical to wires 20, 30, and 40, and the same reference numerals will be used to indicate identical or substantially identical features therebetween.

Referring to FIGS. 6A and 6B, wire 50 generally includes a first section 52, a second section 54 of a different construction than first section 52 as described below, and a third section 56 which may be of the same construction as first section 52. As may be seen from FIG. 6B, first section 52 may include a core 24 made of a uniform material, while second section 54 is formed of an alternating core construction similar to the embodiments described above. In particular, second section 54 is formed of first segments 58 of a first metal, and second segments 60 of a second metal which exhibits a superelastic or shape memory property, such as nitinol, for example.

The superelastic or shape memory properties of nitinol are well known, by which such material may change shape upon heating, such as via application of electrical energy. For example, in one exemplary construction shown in FIG. 6E, the application of electrical energy to wire 50 may cause localized heating in the high electrical resistance periods of the wire thereby causing a pre-defined 90° bend to form in second section 54 of wire 50, for example. In this case, the sections of low relative electrical resistance would dissipate heat less than the high resistance sections in proportion to the electrical resistance ratio and according to simple ohmic heating. Such a feature could be used to stiffen, steer, or otherwise manipulate specific regions of wire 50, and thence may be used to stiffen, steer, or otherwise manipulate any medical devices with which wire 50 is used, such as guide wires, stents, catheters, or other devices.

As discussed above, the wires disclosed herein may include an outer shell made of a first material, and a core comprising a plurality of differing core segments, such as a plurality of core segments of first material and a plurality of core segments of a second material, and optionally, additional core segments of third or more materials. Given the fact that the outer shell 22 may be uniform in construction, in some instances it may be useful to mark the outer shell to indicate the locations of the core segments therewithin based upon a property of the core segments, such as resistance, radiopacity, or any other property.

Referring to FIG. 7, wire 20 of FIG. 1 is again shown, which includes outer shell 22 and core segments 26 and 28 (not visible in FIG. 7) therewithin which are covered by outer shell 22. Core segments 26 may be formed of a relatively conductive material, while core segments 28 may be formed of a relatively resistive material. The locations of core segments 26 and 28 are indicated in FIG. 7 as regions $R_1$ and $R_2$, respectively, though same would not be discernable by viewing of wire 20.

Referring to FIG. 8, one exemplary method of marking outer shell 22 to indicate the locations of core segments 26 and 28 therewithin is illustrated. In this method, electrical current, such as AC or DC voltage, may be applied from current source 70 from first lead 72 to second lead 74 along a given length of wire 20. The application of electrical current to wire will allow the current to pass relatively easily through relatively conductive core segments 26 but will cause resistance within relatively resistive core segments 28. As shown schematically in FIG. 8, core segments 28 will heat, which will in turn heat the portions of outer shell 22 which cover core segments 26. Heating these portions of outer shell 22 will cause oxidation of the material of outer shell 22, causing the material of outer shell 22 to change color on those portions which overly core segments 26. The extent of oxidation, and corresponding color change, observed on the sections of outer shell 22 overlying core segments 26 will vary depending upon the applied current. In this manner, a desired length of wire 20, or the total length of wire 20, may be marked to indicate which sections of wire 20 are conductive and which are resistive, for example.

Referring to FIG. 9, a second method of marking wire 20 which includes varying core segments is illustrated. In this embodiment, one or more properties of one or more of the core segments of the wire may be detected by a continuous process, and outer shell 22 of wire 30 may be marked to indicate the location of one or more core segments. For example, referring to FIG. 9, a power source 70 includes first and second leads 72 and 74 for applying electrical current to a designated section of wire 20 as wire passes power source 70. A feedback loop 76 is provided within the circuit to interface with a controller (not shown) which controls the applied power and determines the electrical resistance as wire passes power source 70. When wire 20 is moved across the location of the circuit and the controller detects a relatively conductive section of wire, the controller may cease application of electrical current. Thereafter, when the controller detects a section of wire having a greater resistance, the circuit may apply a greater amount of power to cause localized heating of the resistive core segments and resulting oxidation and color change of outer core 22 as is described above with respect to the embodiment of FIG. 8. In this manner, wire 20 may be marked on a continuous basis during manufacture to indicate the locations of relatively conductive and relatively resistive core segments therein.

In a further embodiment, a circuit may be configured to detect electrical resistance or any other property of the core segment(s) of wire, such as radiopacity, for example, and may trigger a marking element 78, such as a paint gun, to mark wire 20 and thereby indicate the locations along wire 20 of such segments. For example, if radiopacity is a desired property to be detected, the circuit may be configured to provide an X-ray through wire 20 with feedback loop 76 detecting the presence of relatively radiopaque versus relatively radio translucent sections, with marking element(s) 78 configured to mark either or both of such sections with one or more markings.

Exemplary applications of wires 20 with differing core segments 26 and 28 in accordance with the present invention are set forth below in FIGS. 10A-13D in connection with medical devices.

In FIGS. 10A-10D, an in vivo heating apparatus 100 is shown, which includes wire 20 made in accordance with the present invention, and which extends from proximal end 102 to distal end 104 of device 100. Wire 20 includes outer shell 22 of any suitable biocompatible metal, and core segments 26 and 28 made of different materials. Core segments 26 are made of a material having a relatively low electrical resistance, such as silver, platinum, or tantalum, for example. Core segments 28 are made of a material having a relatively high electrical resistance, such as 300 series stainless steels, cobalt-nickel-chromium-tungsten-iron-manganese alloys, such as L605 alloy, nickel-titanium shape memory alloys, such as NiTiNOL, or cobalt-nickel-chromium alloys, such as MP35N® and 35N LT®, available from Fort Wayne Metals Research Products Corp. of Fort Wayne, Ind.

Wire 20 is twisted or stranded in a double helix, and is formed at distal end 104 of device 100 in an outwardly-splayed fashion to provide a working end 106 of device 100. The ends of wire 20 include anode 108 and cathode 110, respectively, at proximal end 102 of device 100, and device 100 includes an overmolded insulation layer or jacket 112 made of an insulating material such as silicone, Nylon II, or urethane, for example. A temperature measurement feedback device includes a wire 114 extending from proximal end 102 of device 100, where wire 114 is connected to a power source (not shown), to distal end 104 of device 100 through the center of wire 20. Wire 114 terminates in a temperature-sensing probe 116, such as a thermocouple or thermistor, disposed within working end 106 of device 100.

When an electric current is applied across anode 108 and cathode 110 of wire 20, the relatively high electrical resistance of core segments 28 causes same to be heated, in turn causing heating around and within the working end 106 of device 100, with the temperature being sensed by probe 116 to provide feedback to a control unit (not shown) used with device 100. Device 100 may be used in applications such as thermal tissue ablation or cauterization, thermal scar generation and vessel occlusion, for example, to include the Fallopian tubes and sterilization, or for local tissue or fluid heating with feedback control, for example, to heat blood or to warm and dissolve a kidney stone.

Referring to FIGS. 11A-11D, a thermally activated snare device 120 is shown, which includes wire 20 made in accordance with the present invention. The distal end 122 of device 120 is shown in FIG. 11A in section and in a relatively low temperature state, and is shown in FIG. 11D in perspective and a relatively high temperature state. The difference in temperature between states is necessarily sufficient to affect properties in the shape memory or superelastic material. The difference between low and high temperature may vary between 1 and 50° C. depending on the specific application. The proximal end (not shown) of device 120 is connected to a power source (not shown).

Wire includes outer shell 22 and core segments 26 and 28. Outer shell 22 is made of a shape memory alloy, such as a nickel-titanium shape memory alloys, such as NiTiNOL. Core segments 26 are made of a material having a relatively low electrical resistance, such as silver, platinum, or tantalum, for example. Core segment 28 is a single core segment extending through a loop 124 in outer shell 22, and is made of a material having a relatively high electrical resistance, such as 300 series stainless steels, cobalt-nickel-chromium-tungsten-iron-manganese alloys, such as L605 alloy, nickel-titanium shape memory alloys, such as NiTiNOL, or cobalt-nickel-chromium alloys, such as MP35N® and 35N LT®, available from Fort Wayne Metals Research Products Corp. of Fort Wayne, Ind.

In the configuration shown in FIG. 11A, the power source is deactivated and electrical current is not carried through wire 20. In this non-energized or relatively low temperature configuration, the shape memory material of outer shell 22 is shaped such that same forms an open loop 124 at the distal end 122 of device 120. Upon activation of the power source and flow of electrical current through wire 20, core segments 28 are heated to a relatively higher temperature state, causing the shape memory material of outer shell 22 to in turn heat and change to the shape shown in FIG. 11D, in which loop 124 at the distal end 122 of device 120 is closed. Device 120 may be used as a thermally/electrically activated snare to entrap a target device for removal, such as a lesion, for example.

Referring to FIGS. 12A and 12B, a thermally activated linear motion device 130 is shown, for in vivo positioning or mechanical actuation. Device 130 includes a distal end 132 including wire 20 made in accordance with the present invention, having outer shell 22 and core segments 26 and 28. Outer shell 22 is made of a shape memory alloy, such as a nickel-titanium shape memory alloys, such as NiTiNOL. Core segments 26 are made of a material having a relatively low electrical resistance, such as silver, platinum, or tantalum, for example. Core segments 28 are made of a material having a relatively high electrical resistance, such as a 300 series stainless steel, cobalt-nickel-chromium-tungsten-iron-manganese alloys, such as L605 alloy, nickel-titanium shape memory alloys, such as NiTiNOL, or cobalt-nickel-chromium alloys, such as MP35N® and 35N LT®, available from Fort Wayne Metals Research Products Corp. of Fort Wayne, Ind. The proximal end (not shown) of device 130 is connected to a power source (not shown).

Device 130 has an initial nominal length $D_1$, measured from a given point on device 130 to the tip of device 130. In the configuration shown in FIG. 12A, the power source is deactivated and electrical current is not carried through wire 20. In this non-energized or relatively low temperature configuration, the shape memory material of outer shell 22 is as shown in FIG. 12A, in which the material is relatively straight or alternatively, is linearly elongated. Upon activation of the power source and flow of electrical current through wire 20, core segments 28 are heated to a relatively higher temperature state, causing the shape memory material of outer shell 22 to in turn heat and change to the shape shown in FIG. 12D, in which the material is bent as shown in FIG. 12D or alternatively, is linearly reduced in length. The reduction in length reduces the nominal length by dimension A to a reduced nominal length $D_2$. Alternatively, the configuration of device 130 may change from that shown in FIG. 12D to that shown in FIG. 12A upon application of electrical current, i.e., device 130 may be designed to extend in length upon application of electrical current.

Exemplary applications of device 130 include applications in which a positional adjustment of an implant device, such as a stent, for example, is desired within a precise, defined dimensional range. In one embodiment, several devices 130 may be provided in a kit, with the devices designed or calibrated to provide respective dimensional changes A in known increments, such as 1 mm, 5 mm, or 10 mm, for example. A medical practitioner may select a particular device 130 from the kit which has the desired nominal adjustment increment for use in a particular application based on medical imaging data, for example.

Figure 13A:
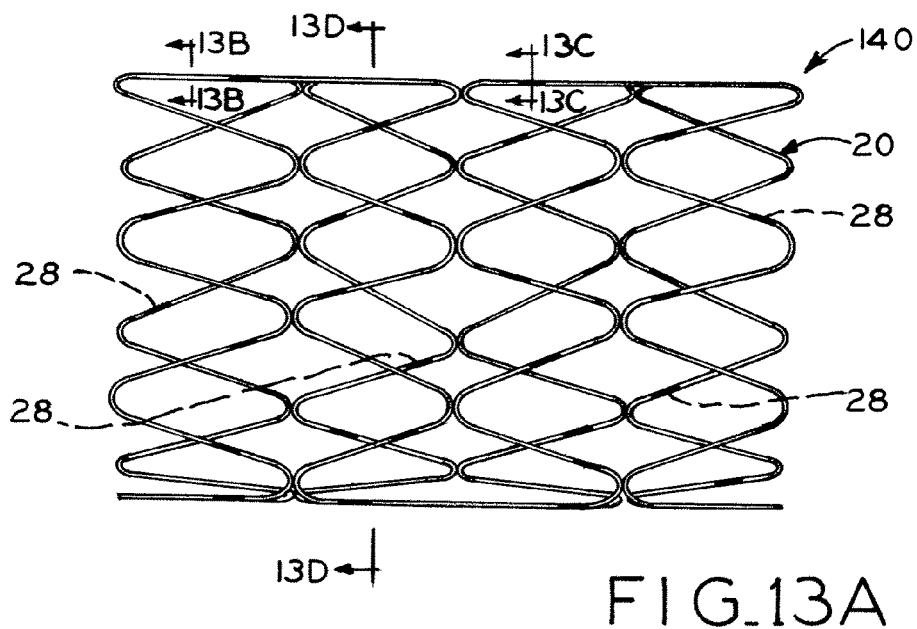
FIG. 13A is a perspective view of a tissue scaffold or stent including a wire made in accordance with the present invention.
Figure 13B:
FIG. 13B is a sectional view taken along line 13B-13B of FIG. 13A.
Figure 13C:
FIG. 13C is a sectional view taken along line 13C-13C of FIG. 13A.
Figure 13D:
FIG. 13D is a sectional view taken along line 13D-13D of FIG. 13A.

Referring to FIGS. 13A-13D, a tissue scaffold or vessel stent device 140 is shown which is made from one or more wires 20 in accordance with the present invention, which are looped together to form the cylindrical cross-sectional shape of device 140 as shown in FIGS. 13A and 13B. Wire 20 includes an outer shell 22 made of 300 series stainless steels, cobalt-nickel-chromium-tungsten-iron-manganese alloys, such as L605 alloy, nickel-titanium shape memory alloys, such as NiTiNOL, or cobalt-nickel-chromium alloys, such as MP35N® and 35N LT®, available from Fort Wayne Metals Research Products Corp. of Fort Wayne, Ind. Core segments 26 comprise the majority portion of the core of wire 20, and are made of a radio-translucent material, such as NiTiNOL, for example. Core segments 28 comprise the minority portion of the core of wire 20, and are made of a radio-opaque material, such as platinum, tantalum, niobium, palladium, tungsten, or a platinum/iridium alloy, for example. In this manner, the relatively more expensive radio-opaque material is conserved in the device, while still providing a number of relatively short, periodic segments of radio-opacity for visualization of device 140 in medical imaging such as fluoroscopy, for example, as schematically indicated by the darker areas in wire 20 of device 140 in FIG. 13A. In addition, an increase in the performance and/or the radial force of the scaffold or stent device 140 may be improved due to a greater net proportion of core segments 26 over a majority of the length of wire 20.

Figures 14A, 14B:
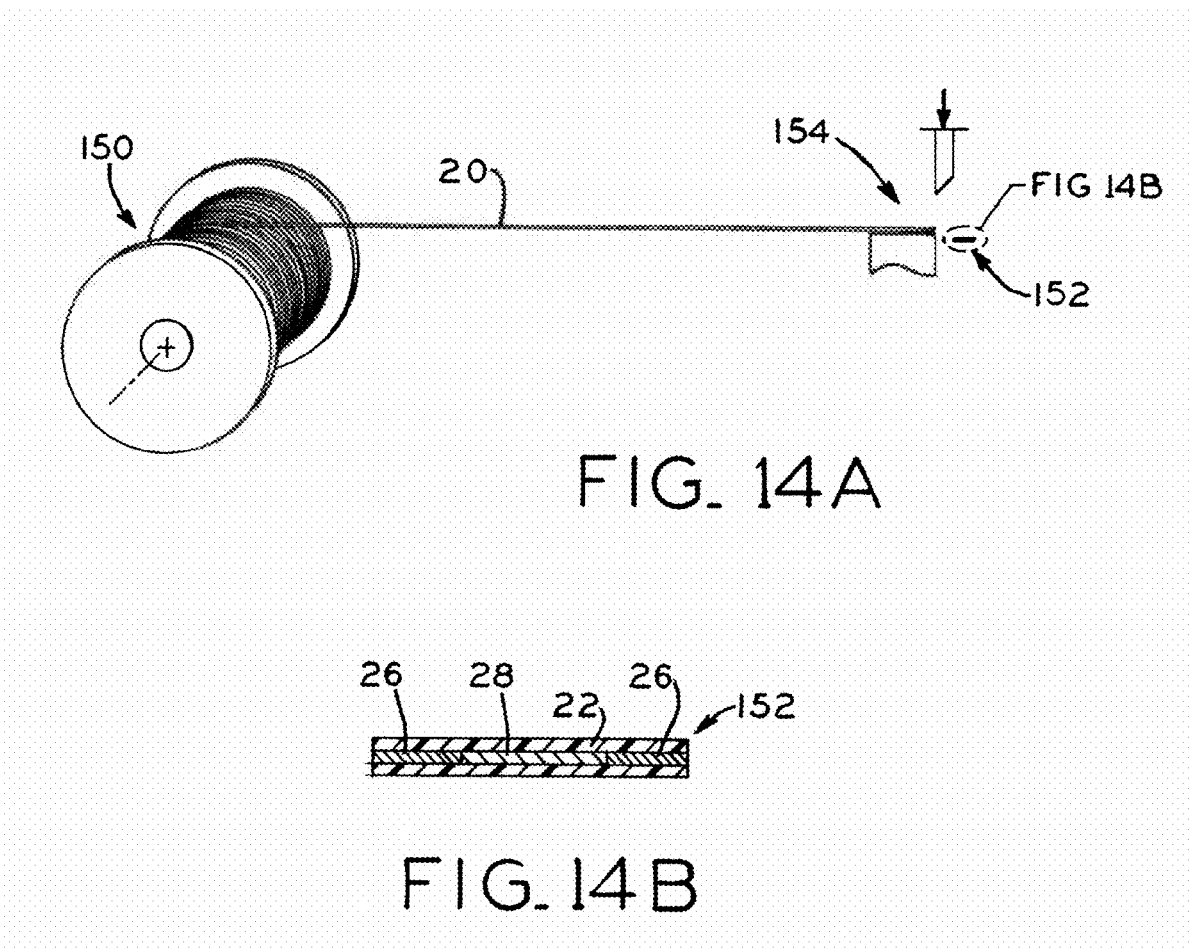
FIG. 14A is a perspective view showing the manufacture of individual wire segments from a long wire, each made in accordance with the present invention.
FIG. 14B is a fragmentary view of a wire segment obtained from the wire of FIG. 14A.

Advantageously, referring to FIGS. 14A and 14B, with the present method, an elongated length wire 20 may be formed by drawing processes as described above and in the Examples below, having a periodic alternating arrangement of core segments 26 and 28. This wire 20 may be manufactured by drawing, as described above, and wound onto a spool 150, as shown in FIG. 14A, for example, for shipping or storage, with the wire 20 having a very long length, such as tens or hundreds of meters, for example. Then, individual wire portions or segments 152 may be cut from the wire 20 by a cutting or separating device 154, with each wire segment 152 having a desired number and arrangement of periodically alternating core segments 26 and 28 as shown in FIG. 14B for use in a desired application, such as those described above. In this manner, manufacture of a large number of individual wire portions or segments 152 of alternating core construction is facilitated by initial manufacture of a very long continuous wire 20 as described above, which may also be marked as described above and in the Examples below, followed by cutting the individual wire portions or segments 152.

EXAMPLES

Example 1

Production of an Alternating Core Composite Wire

In this Example, an alternating core composite wire was made in accordance with the present invention, including an outer shell made of MP35N alloy, specifically, 35N LT® alloy, available from Fort Wayne Metals Research Products Corporation of Fort Wayne, Ind. This material is described in further detail in the above-incorporated U.S. patent application Ser. No. 10/656,918. The outer shell had an initial outer diameter of 0.144 inches (0.366 cm) and an initial inner diameter of 0.098 inches (0.249 cm).

Two different types of core segments were used, made of 304V stainless steel and of 99.95% silver, respectively, with the wire including thirty (30) individual core segments of each of these materials. The 304V stainless steel core segments had an initial outer diameter of 0.064 inches (0.163 cm), with each segment ranging in length from 0.060 inches (0.152 cm) to 0.080 inches (0.203 cm). The 99.95% silver core segments had an initial outer diameter of 0.088 inches (0.224 cm), with each segment ranging in length from 0.20 inches (0.508 cm) to 0.25 inches (0.635 cm). The core segments were loaded into the outer shell in an alternating periodic arrangement of [A-B-A-B- . . . ].

The wire was successively drawn using 10-12 degree reduction angle diamond dies, with a nominal 20% area of reduction between each draw. Following each draw, the wire was annealed at 927° C. in a furnace under a hydrogen atmosphere with a 30 second dwell time for each anneal. The draw schedule for the wire is set forth in Table 2 below.

TABLE 2

| Draw | Outer diameter (inches) |
|---|---|
| — | 0.144 (0.366 cm) |
| 1 | 0.128 (0.325 cm) |
| 2 | 0.102 (0.259 cm) |
| 3 | 0.064 (0.163 cm) |
| 4 | 0.0453 (0.115 cm) |
| 5 | 0.032 (0.081 cm) |
| 6 | 0.0266 (0.0676 cm) |
| 7 | 0.0159 (0.0404 cm) |
| 8 | 0.0113 (0.0287 cm) |
| 9 | 0.0089 (0.023 cm) |
| 10 | 0.0063 (0.016 cm) |
| 11 (final) | 0.005 (0.013 cm) |

In the first draw, the wire was drawn from an outer diameter of 0.144 inches (0.366 cm) to an outer diameter of 0.128 inches (0.325 cm), using a back support rod as described above, and the outer shell closed on the silver core segments. The back support rod was not used in subsequent draws. In the second draw, the wire was drawn from an outer diameter of 0.128 inches (0.325 cm) to an outer diameter of 0.102 inches (0.259 cm), and the outer shell closed on the stainless steel core segments.

An alternate draw schedule, which includes less cold work in the early stage draws, is set forth in Table 3 below:

TABLE 3

| Draw | Outer diameter (inches) |
|---|---|
| — | 0.144 (0.366 cm) |
| 1 | 0.128 (0.325 cm) |
| 2 | 0.102 (0.259 cm) |
| 3 | 0.081 (0.206 cm) |
| 4 | 0.064 (0.163 cm) |
| 5 | 0.0508 (0.129 cm) |
| 6 | 0.0359 (0.0912 cm) |
| 7 | 0.0253 (0.0643 cm) |
| 8 | 0.0179 (0.0454 cm) |
| 9 | 0.0126 (0.032 cm) |
| 10 | 0.0089 (0.023 cm) |
| 11 | 0.0063 (0.016 cm) |
| 12 (final) | 0.005 (0.013 cm) |

In Table 4 below, outer diameters of the wire are given, most of which correspond to the outer diameters of the wire provided in the draw schedule of Table 2 above. In Table 4, the minimum and maximum lengths of the silver and stainless steel core segments have been calculated based on the wire outer diameters and the calculations outlined in the above description.

TABLE 4

| Wire Outer Diameter (inches) | Length increase after dense contact [(D/d)^2] (inches) | Ag core segment length, (MIN) (feet) | Ag core segment length, (MAX) (feet) | Stainless steel core segment length, (MIN) (feet) | Stainless steel core segment length, (MAX) (feet) |
|---|---|---|---|---|---|
| 0.134 (0.340 cm) | | 0.017 (0.005 m) | 0.021 (0.006 m) | 0.0050 (0.002 m) | 0.0067 (0.002 m) |
| 0.11 (0.279 cm) | 1.484 (3.769 cm) | 0.025 (0.008 m) | 0.031 (0.009 m) | 0.0050 (0.002 m) | 0.0067 (0.002 m) |
| 0.072 (0.183 cm) | 2.334 (5.928 cm) | 0.058 (0.018 m) | 0.072 (0.022 m) | 0.012 (0.004 m) | 0.016 (0.001 m) |
| 0.064 (0.163 cm) | 1.266 (3.216 cm) | 0.073 (0.022 m) | 0.091 (0.028 m) | 0.015 (0.005 m) | 0.020 (0.006 m) |
| 0.0453 (0.115 cm) | 1.996 (5.070 cm) | 0.15 (0.046 m) | 0.18 (0.055 m) | 0.029 (0.009 m) | 0.039 (0.012 m) |
| 0.032 (0.081 cm) | 2.004 (5.090 cm) | 0.29 (0.088 m) | 0.37 (0.113 m) | 0.059 (0.018 m) | 0.079 (0.024 m) |
| 0.0226 (0.0574 cm) | 2.005 (5.093 cm) | 0.59 (0.180 m) | 0.73 (0.223 m) | 0.12 (0.037 m) | 0.16 (0.049 m) |
| 0.0159 (0.040 cm) | 2.020 (5.131 cm) | 1.2 (0.366 m) | 1.5 (0.457 m) | 0.24 (0.073 m) | 0.32 (0.098 m) |
| 0.0113 (0.029 cm) | 1.980 (5.029 cm) | 2.3 (0.701 m) | 2.9 (0.884 m) | 0.47 (0.143 m) | 0.63 (0.192 m) |
| 0.0089 (0.023 cm) | 1.612 (4.094 cm) | 3.8 (1.158 m) | 4.7 (1.433 m) | 0.76 (0.232 m) | 1.02 (0.311 m) |
| 0.0063 | 1.996 | 7.5 | 9.4 | 1.5 | 2.0 |

TABLE 4-continued

| Wire Outer Diameter (inches) | Length increase after dense contact [(D/d)^2] (inches) | Ag core segment length, (MIN) (feet) | Ag core segment length, (MAX) (feet) | Stainless steel core segment length, (MIN) (feet) | Stainless steel core segment length, (MAX) (feet) |
|---|---|---|---|---|---|
| (0.016 cm) | (5.070 cm) | (2.286 m) | (2.865 m) | (0.457 m) | (0.610 m) |
| 0.005 | 1.588 | 12.0 | 15.0 | 2.4 | 3.2 |
| (0.013 cm) | (4.034 cm) | (3.658 m) | (4.572 m) | (0.732 m) | (0.975 m) |

As set forth in Table 4 above, for the final wire having an outer diameter of 0.005 inches (0.013 cm), the silver core segments are expected to range between 12.0 feet (3.658 m) and 15.0 feet (4.572 m) in length, and the stainless steel core segments are expected to range between 2.4 feet (0.732 m) and 3.2 feet (0.975 m) in length. Thus, the period length, i.e., the sum of the lengths of one silver core segment plus one stainless steel core segment, is expected to range between 14.4 feet (4.389 m) and 18.2 feet (5.547 m).

Example 2

Evaluation of an Alternating Core Composite Wire

In this Example, the wire formed in Example 1 was tested to validate the predicted segment length of the core segments of the wire and to mark the wire to indicate the presence of the various different core segments within the wire.

A 30 ft. (9.144 m) segment of the wire of Example 1 was stretched out and suspended in air. Then, the wire segment was contacted with electrical conductive clips and connected across a 115/120V, 60 Hz electrical power source. The high resistance sections of the wire, namely, the stainless steel core segments, heated sufficiently to create a brown oxide layer on the portions of the outer shell surrounding these segments, thereby indicating the presence of the stainless steel core segments beneath the outer shell. The portions of the outer shell surrounding the low resistance sections of the wire, namely, the silver core segments, maintained their as-drawn silvery luster, thereby indicating the presence of silver core segments beneath the outer shell. This method provided an easy visual discernment of the presence of the silver and the stainless steel core segments beneath their respective portions of the outer shell.

Then, the wire segment was cut into segments, each 12 inches (30.4 cm) in length, and the direct current electrical resistance and ultimate tensile strength of each section was tested. The electrical resistance was measured using a temperature-compensated, four wire resistance measurement bridge, available from Valhalla Scientific, Inc. The ultimate tensile strength was tested using a tensile strength test device, available from Instron, Inc., by clamping the ends of each segment in the hydraulic grips of the device and applying a monotonically increasing pull force to the sections until rupture.

The results of the foregoing tests are shown below in Table 5 and are plotted in FIG. 15.

TABLE 5

| Segment # | Distance/location along the wire (feet) | Resistance (ohm/ft) | Ultimate Tensile Strength (×10³ psi) |
|---|---|---|---|
| 1 | 0 | 1.072 | 191 |
| 2 | 1 | 1.039 | 189 |
| 3 | 2 | 1.081 | 193 |
| 4 | 3 | 1.099 | 193 |
| 5 | 4 | 1.113 | 193 |
| 6 | 5 | 1.151 | 196 |
| 7 | 6 | 1.306 | 209 |
| 8 | 7 | 9.48 | 239 |
| 9 | 7.5 | 18 | 245 |
| 10 | 8 | 18.14 | 251 |
| 11 | 8.5 | 17.3 | 248 |
| 12 | 9 | 5.88 | 230 |
| 13 | 10 | 1.15 | 195 |
| 14 | 11 | 1.072 | 193 |
| 15 | 12 | 1.039 | 191 |
| 16 | 13 | 1.081 | 193 |
| 17 | 14 | 1.072 | 193 |
| 18 | 15 | 1.072 | 193 |
| 19 | 16 | 1.081 | 195 |
| 20 | 17 | 1.065 | 193 |
| 21 | 18 | 1.075 | 193 |
| 22 | 19 | 1.081 | 193 |
| 23 | 20 | 1.151 | 196 |
| 24 | 21 | 1.306 | 209 |
| 25 | 22 | 9.48 | 239 |
| 26 | 22.5 | 17.5 | 246 |
| 27 | 23 | 18.14 | 251 |
| 28 | 23.5 | 17.5 | 249 |
| 29 | 24 | 5.88 | 230 |
| 30 | 25 | 1.15 | 195 |
| 31 | 26 | 1.072 | 193 |
| 32 | 27 | 1.039 | 191 |
| 33 | 28 | 1.081 | 193 |

Figure 15:
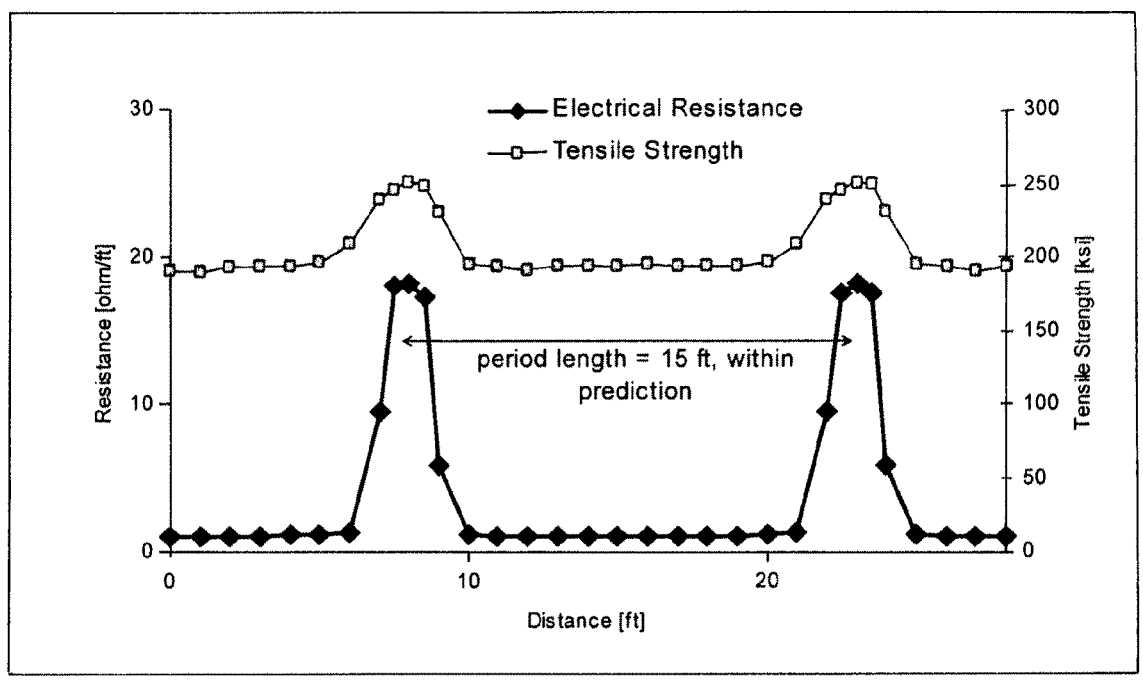
FIG. 15 is a plot of electrical resistance and ultimate tensile strength of segments of a wire made in Example 1.

As may be seen from the data in Table 5 and from FIG. 15, the portions of the wire having higher electrical resistance and higher ultimate tensile strength indicate the presence of the stainless steel core segments in the wire, while the portions of the wire having lesser electrical resistance and lesser ultimate tensile strength indicate the presence of the silver core segments. In FIG. 15, the period length was measured between the centers of the curves of higher electrical resistance, and thereby indicates the distance between the central portions of a pair of successive stainless steel core segments. This period length was calculated to be 15 feet (4.572 m), within the predicted range of 14.4 feet (4.389 m) to 18.2 feet (5.547 m) as calculated in Example 1 above.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A wire, comprising:
   an outer shell made of a biocompatible metal; and
   a core disposed within said outer shell, said core including a plurality of first core segments made of a first material and at least one second core segment made of a second material different from said first material, said first core segments and said at least one second core segment arranged in a periodic alternating arrangement along a length of said wire, each of said first core segments and said at least one second core segment completely filling said outer shell.

2. The wire of claim 1, wherein said core includes a plurality of said first core segments and a plurality of said second core segments.

3. The wire of claim 2, wherein said first core material is a metal and said second core material is a polymeric material.

4. The wire of claim 1, wherein said core comprises at least two of said first core segments (A) and at least two of said second core segments (B), said core segments arranged in a periodic alternating arrangement represented by [A-B-A-B- . . . ].

5. The wire of claim 1, wherein said first and second core materials are first and second different metals or metal alloys.

6. The wire of claim 1, wherein said first core material is a first metal or metal alloy having a relatively low electrical resistance, and said second core material is a second metal or metal alloy different from said first metal or metal alloy and having a relatively high electrical resistance.

7. A wire, comprising:
   an outer shell made of a biocompatible metal; and
   a core disposed within said outer shell, said core including a plurality of first core segments made of a first material and at least one second core segment made of a second material different from said first material, said first core segments and said at least one second core segment arranged in a periodic alternating arrangement along a length of said wire, wherein said outer shell includes an inner diameter and said first core segments and said at least one second core segment each include an outer diameter equal to said inner diameter of said outer shell whereby, when viewed in section, each of said core segments completely fills said outer shell.

8. The wire of claim 7, wherein said core includes a plurality of said first core segments and a plurality of said second core segments.

9. The wire of claim 7, wherein said core comprises at least two of said first core segments (A) and at least two of said second core segments (B), said core segments arranged in a periodic alternating arrangement represented by [A-B-A-B- . . . ].

10. The wire of claim 7, wherein said first and second core materials are first and second different metals or metal alloys.

11. The wire of claim 7, wherein said first core material is a metal and said second core material is a polymeric material.

12. The wire of claim 7, wherein said first core material is a first metal or metal alloy having a relatively low electrical resistance, and said second core material is a second metal or metal alloy different from said first metal or metal alloy and having a relatively high electrical resistance.

13. A method of manufacturing a wire, comprising the steps of:
   providing an outer shell made of a biocompatible metal;
   inserting a plurality of first core segments and at least one second core segment into the outer shell to form a wire construct, the first core segments and the at least one second core segment disposed in a periodic alternating arrangement along a length of the outer shell; and
   drawing the wire construct from a first outer diameter to a second outer diameter less than the first outer diameter until the outer shell includes an inner diameter and the first core segments and the at least one second core segment each include an outer diameter equal to the inner diameter of the outer shell whereby, when viewed in section, each of the core segments completely fills the outer shell.

14. The method of claim 13, wherein said inserting step further comprises inserting a plurality of first core segments and a plurality of second core segment into the outer shell.

15. The method of claim 13, wherein the first core segments and the at least one second core segment are made of different materials.

16. The method of claim 15, wherein the material of the first core segments is a first metal or metal alloy having a relatively low electrical resistance, and the material of the at least one second core segment is a second metal or metal alloy different from the first metal or metal alloy and having a relatively high electrical resistance.

17. The method of claim 13, wherein said drawing step comprises drawing the wire through a die along a first direction from an upstream side of the die to a downstream side of the die.

18. The method of claim 17, wherein said drawing step further comprises:
   drawing the wire construct in at least one initial draw to progressively engage an inner surface of the outer shell with the outer surfaces of each of the core segments to form a wire with the inner surface of the outer shell in contact with the outer surfaces of each of the core segments; and
   drawing the wire in a plurality of finishing draws to progressively reduce the outer diameter of the wire.

19. The method of claim 18, wherein said step of drawing the wire construct in at least one initial draw further comprises applying a force against the core segments along the first direction on the upstream side of the die.

20. The method of claim 19, wherein said drawing step further comprises applying a force against the core segments using a rod, the rod inserted within the outer shell and contacting a core segment.

21. The method of claim 18, further comprising the additional step of separating the wire in to a plurality of individual wire segments, each wire segment comprising:
   a section of the outer shell; and
   a core disposed within the section of the outer shell, the core including portions of at least two of the first core segments, and at least one of the second core segments.

22. The method of claim 13, further comprising the additional step of separating the wire into a plurality of individual wire segments, each wire segment comprising:
   a section of the outer shell; and
   a core disposed within the section of the outer shell, the core including portions of at least two of the first core segments, and at least one of the second core segments.

* * * * *